United States Patent
Fournier

(10) Patent No.: US 6,365,103 B1
(45) Date of Patent: Apr. 2, 2002

(54) METHOD FOR STERILIZING AN ENDOSCOPE

(75) Inventor: Stephane Fournier, Levis (CA)

(73) Assignee: Technologies of Sterilization with Ozone TSO3 Inc. (CA)

(*) Notice: Subject to any disclaimer, the term of this patent is extended or adjusted under 35 U.S.C. 154(b) by 0 days.

(21) Appl. No.: 09/506,262

(22) Filed: Feb. 17, 2000

(30) Foreign Application Priority Data

Feb. 11, 2000 (CA) .............................................. 2298165

(51) Int. Cl.[7] .................................................. A61L 2/20

(52) U.S. Cl. ........................ 422/33; 422/116; 422/300

(58) Field of Search .................................. 422/33, 116

(56) References Cited

U.S. PATENT DOCUMENTS

| | | | |
|---|---|---|---|
| 4,862,872 A | | 9/1989 | Yabe et al. |
| 5,133,336 A | | 7/1992 | Savitt et al. |
| 5,266,275 A | * | 11/1993 | Faddis ........................ 422/116 |
| 5,297,537 A | | 3/1994 | Savitt et al. |
| 5,334,355 A | | 8/1994 | Faddis |
| 5,344,622 A | | 9/1994 | Faddis et al. |
| 5,534,221 A | * | 7/1996 | Hillebrenner et al. ......... 422/33 |
| 5,634,880 A | | 6/1997 | Feldman et al. |
| 5,667,753 A | | 9/1997 | Jacobs et al. |
| 5,868,999 A | | 2/1999 | Karlston ....................... 422/30 |
| 5,876,331 A | | 3/1999 | Wu et al. |

FOREIGN PATENT DOCUMENTS

| | | | |
|---|---|---|---|
| CA | 2176907 | * | 5/1996 |
| CA | 2176907 | | 11/1996 |
| CA | 2220667 | | 5/1998 |
| FR | 2759590 | | 8/1998 |
| JP | 200024094 A | | 1/2000 |
| WO | WO 99/53966 | | 10/1999 |
| WO | WO 00/66186 | | 11/2000 |

OTHER PUBLICATIONS

Ishizaki et al., 1986. Inactivation of the Bacillus Sores by Gaseous Ozone, J. Appl. Bacterial, 60:67–72.*
Encyclopaedia Of Chemical Technology, vol. 17, Ozone p. 953 to 964.
Ishizaki et al., 1986. Inactivation of the Bacillius spores by gaseous ozone, *J. Appl. Bacterial*, 60:67–72.
Langlais et al., (EDS), 1991, Ozone in Water Treatment, Application and Engineering, Louis Publishers: Chelsea, Michigan, pp. 11–23.

* cited by examiner

*Primary Examiner*—Robert J. Warden, Sr.
*Assistant Examiner*—Sean E. Conley
(74) *Attorney, Agent, or Firm*—Brinks, Hofer, Gilson & Lione

(57) ABSTRACT

A method of sterilizing a hollow endoscope having a conduit is disclosed. An end of the endoscope conduit is connected to a sealed vessel such that the endoscope conduit is in fluid communication with the sealed vessel. The endoscope is placed in a sterilization chamber and the chamber sealed. The sterilization chamber is run through sterilization cycles in which the pressure within the chamber is varied. During the pressure variation within the sterilizing chamber, sterilizing gas is drawn from the sterilizing chamber via the endoscope conduit into the vessel. During the pressure variation the inner surface of the endoscope is subjected to sterilizing conditions in addition to the outer surface of the endoscope. In a preferred embodiment the sterilizing conditions are provided for by ozone gas in the presence of a humid atmosphere of at least 95% water saturation. The sterilization process is operatively simple and reduces the chance of human errors caused by false interpretation and handling. The ozone sterilization method of the invention requires substantially no aeration or cooling down of sterilized instruments so that they can be used immediately following the sterilization cycle. The present invention permits hospitals to reduce the costs associated with maintaining an expensive endoscope inventory.

16 Claims, 4 Drawing Sheets

METHOD FOR STERILIZING AN ENDOSCOPE

FIELD OF THE INVENTION

The invention relates to a method of sterilizing endoscopes and in particular hollow endoscopes.

BACKGROUND OF THE INVENTION

The development of endoscopic instruments has greatly advanced the ability of the medical profession to diagnose and treat diseases in relatively inaccessible regions of the body. The first examinations that could be considered "endoscopic" in the modern sense were probably the rectal inspections conducted in the 18th century. The physician peered through a rigid tube inserted into the patient's rectum and relied on candles or gas lamps to illuminate the interior. By today's standards the physician saw very little; however, endoscopic examinations continued and endoscopes of various designs were invented and have revolutionized many medical procedures.

As is well known to one skilled in the art, endoscope tubes often include mechanisms for turning the tip in four directions, up, down and from side to side, to facilitate passage of the instrument around angles and allow visualization of all surfaces. An additional viewing channel, coupled to a separate eye piece, for simultaneous direct viewing by a second observer is also available. In addition, the tubes contain channels for air insufflation and water instillation, so that lenses can be cleaned during a procedure, and to allow passage of biopsy instruments and fulguration instruments. Tube channels may also be provided for passage of light from a laser for ablation/photo dynamic therapy, spray catheters, polypectomy snare wires etc.

A typical endoscope, as found in a physician's office or hospital, is used repeatedly. Thus, it is imperative that endoscopic tubes must be completely sterilized between each use to avoid the transmission of diseases, such as AIDS, Hepatitis, etc. Typically, a sterilization fluid is passed through the water and air ducts of the instrument to sterilize the internal surfaces. This sterilization fluid is at times supplied from a bottle which temporarily replaces the water bottle used with the endoscope. As is evident to one skilled in the art, conduits (internal surfaces) within the endoscope are the most difficult parts of the endoscope to sterilize. Endoscopic materials are also often heat sensitive and do not lend themselves to heat sterilization techniques.

In light of the ubiquitous use of the endoscope by the medical profession and intricate internal surfaces of the endoscope, an efficient method for sterilizing the endoscope at ambient temperatures is required.

U.S. Pat. No. 4,862,872 issued to Yabe et al. on Sep. 5, 1989 discloses an endoscope and a washing apparatus for an endoscope. The endoscope comprises an elongate insertable part having an observation window and illuminating window in the tip part, an observation means for observing an object by receiving a returning light from the object which enters through the observing window, an illuminating light output means emitting an illuminating light from the illuminating window and a memorizing means capable of memorizing the information on washing. The washing apparatus is provided with a read-out means for reading out the information memorized by the memorizing means of the above mentioned endoscope and a control means controlling the conditions of washing the above mentioned endoscope by the information read out by this read-out means. This endoscope washing apparatus is relatively complex and likely expensive to manufacture.

U.S. Pat. No. 5,297,537 issued to Savitt et al. on Mar. 29, 1994 discloses a disposable liquid supply kit for use with an endoscope that comprises a closed liquid container for connection to an endoscope prior to use. With a disposable unit of this type, a fresh supply of sterile water is installed in the endoscope between each use with a patient. The liquid supply system is preferably sealed at the factory to insure complete sterilization. Obviously, a medical facility using such a kit requires inventory and incurs expense as a result of maintaining and monitoring the inventory.

U.S. Pat. No. 5,534,221 issued to Hillebrenner et al. on Jul. 9, 1996 entitled "Device and system for sterilizing objects" discloses a hollow cassette for holding an item to be sterilized, for example an endoscope. The cassette is a sealable cassette in which an endoscope or other medical device is placed. The cassette has input and output fluid sealing ports for the introduction and removal of a sterilizing fluid. The cannula of the endoscope is coupled either to the input or output port. The cassette is formed of two identical halves which are placed in superimposed sealable relationship with each other to form a hollow chamber. A latch is placed on one or more handles on the cassette to create a presealing condition to allow a vacuum to be introduced at the outlet port. The cassette is then placed in an outer oven-like container or warming chamber where the temperature is properly maintained. Connections are made to open the input and output ports on the cassette such that the sterilizing agent may be introduced through a first port to bathe the outside of the medical endoscope, while one end of the endoscope is coupled to the output port where a vacuum is supplied external to the cassette to pull the sterilization agent into the cassette and through the interior passageways of the endoscope. When the sterilization process is completed, the warming chamber is opened and the sterilizing cassette is simply removed from the chamber with the input and output ports being uncoupled from their respective sources. A tight seal is maintained and the object remains in the sterilized interior of the cassette until the cassette is opened or the device is to be used. This represents a sterilization system which is relatively costly to produce and use.

It would be advantageous to provide a method for endoscopic sterilization that is inexpensive and operatively simple. It would also be advantageous to provide a method that can be used with a sterilizing chamber that is used to sterilize many different articles and not just for endoscopic sterilization per se. It has now been found that by applying principles of pressure equilibration it is possible for an endoscope's conduit(s) and external surfaces to be sterilized.

Conventional sterilization procedures for medical instruments involve high temperature (such as steam and dry heat units) or toxic chemicals (such as ethylene oxide gas, EtO). Steam pressure sterilization has been the time-honoured method of sterilization. It is fast and cost effective. However, the autoclave destroys heat-sensitive instruments such as arthroscopes and endoscopes.

Ethylene oxide sterilization is used to cold-sterilize heat-sensitive instruments and can be used as a sterilization gas. However, it has been deemed by national health and safety organizations to be carcinogenic and neurotoxic, and requires long sterilization and aeration periods.

Ozone is a more efficient, safer, and less expensive sterilization agent and is easily generated from oxygen, preferably hospital grade oxygen. Ozone is widely used in industry as an oxidising agent to bleach paper pulp, treat drinking water, and sterilize sewage water and food products. Ozone generally acts on chemical compounds in two ways. Either by direct reaction or through hydroxyl radical species formed during the decomposition of ozone (Encyclopaedia Of Chemical Technology, Vol. 17, Ozone page 953 to 964). The amounts (concentrations) of ozone required in the sterilization gas for water purification are low, generally less than 36 mg/l (milligram per liter). Significantly higher concentrations are required to make ozone gas an effective sterilant of micro-organisms, and those high concentrations of ozone gas are generally combined with critical levels of humidity during the entire sterilization cycle to improve sterilization efficiency. The activity of ozone increases rapidly with increased relative humidity. The resistance of spores to ozone varies from strain to strain, but the differences become comparatively small at high relative humidity (Ishizaki et al., 1986. Inactivation of the Silas spores by gaseous ozone, *J. Appl Bacterial*, 60:67–72), a high relative humidity is required for the ozone to penetrate the protective shells of micro-organisms. The presence of water often accelerates ozone reactions with organic substances (Langlais et al., (EDS), 1991, Ozone in Water Treatment, Application and Engineering. Louis Publishers: Chelsea, Mich., 569 pages). Thus, ozone containing gas can also be used as a sterilizing agent for endoscopes, especially when combined with high humidity.

Water evaporates at 100° C. at atmospheric pressure (1013 mbar). Thus, various prior patents (see Faddis et al., U.S. Pat. Nos. 5,266,275; 5,334,355; and 5,334,622) teach sterilization systems wherein water is heated to above the boiling point (100° C. at 1013 mbar) to evaporate the water for injection into the ozone-containing gas produced by an ozone generator. The steam is heated to 120° C. prior to injection into the ozone-containing gas. However, since the decomposition of ozone increases exponentially with temperature in the range of 20 to 300° C., injecting the water vapour at a temperature of about 120° C. leads to premature ozone decomposition. A more efficient and effective sterilization apparatus for the sterilization of ozone at a relative humidity above at least 95% is disclosed in our co-pending U.S. patent application Ser. No. 09/310,695 which is incorporated herein in its entirety.

SUMMARY OF THE INVENTION

It is an object of the present invention to provide a method for the sterilization of a hollow endoscope.

It is another object of the invention to provide a sterilization method for an endoscope in which the sterilization is carried out with a sterilizing gas, for example an ozone-containing gas, preferably humidified ozone-containing gas, having a temperature of 20° C. to 35° C.

Endoscopes are available that do not have passages through which a fluid may pass. Nevertheless, the majority of endoscopes have at least one passage through the endoscope. The present invention provides a method of sterilizing endoscopes with internal passages, i.e., hollow endoscopes.

As one skilled in the art will appreciate, it is possible to disassemble an endoscope into sections. Methods for sterilizing an "endoscope" as disclosed herein are applicable to both assembled endoscopes and sections thereof. Hence, the term "endoscope" as used herein is to be construed as encompassing hollow endoscope sections.

In accordance with the present invention there is provided a method for sterilizing within a sterilization chamber a hollow endoscope having an internal passage having an internal volume comprising the steps of:

(i) sealing the endoscope to a sealed vessel for fluid communication between the passage and the vessel to form an endoscope-vessel combination, said vessel having an internal volume;

(ii) disposing the endoscope-vessel combination within the sterilization chamber;

(iii) supplying a sterilization gas;

(iv) effecting a pressure difference between the internal volume of the vessel and the sterilizing chamber, the pressure in the sterilizing chamber and the internal volume of the vessel selected such that sterilizing gas supplied to the sterilizing chamber flows through the internal passage of the endoscope into the vessel.

Preferably the end of the endoscope which is sealed in fluid communication with said vessel, protrudes into said vessel.

In accordance with a further preferred embodiment of the present invention there is provided a method for sterilizing within a sterilization chamber a hollow endoscope having a distal end, a proximal end and an internal passage having an internal volume comprising the steps of:

(i) providing a sterilization chamber;

(ii) sealing the distal end of the endoscope in fluid communication with a substantially closed vessel to form an endoscope-vessel combination, said vessel having an internal volume larger than the internal volume of the endoscope;

(iii) placing the endoscope-vessel combination into the sterilization chamber;

(iv) sealing the sterilization chamber;

(v) applying a vacuum of a preselected vacuum pressure to the sterilization chamber;

(vi) supplying an amount of water vapour to the sterilization chamber for humidifying the sterilization chamber;

(vii) supplying ozone to the sterilization chamber at a higher pressure than said pre-selected vacuum pressure, said ozone being sufficient to sterilize the endoscope and the internal passage of the endoscope; and (viii) maintaining the endoscope, the internal volume of the endoscope and the internal volume of the vessel in contact with the ozone for a preselected treatment period to sterilize the endoscope

BRIEF DESCRIPTION OF THE DRAWINGS

The invention will be described in more detail in the following by way of example only and with reference to the attached drawings, wherein.

DETAILED DESCRIPTION OF THE INVENTION

Figure 1:
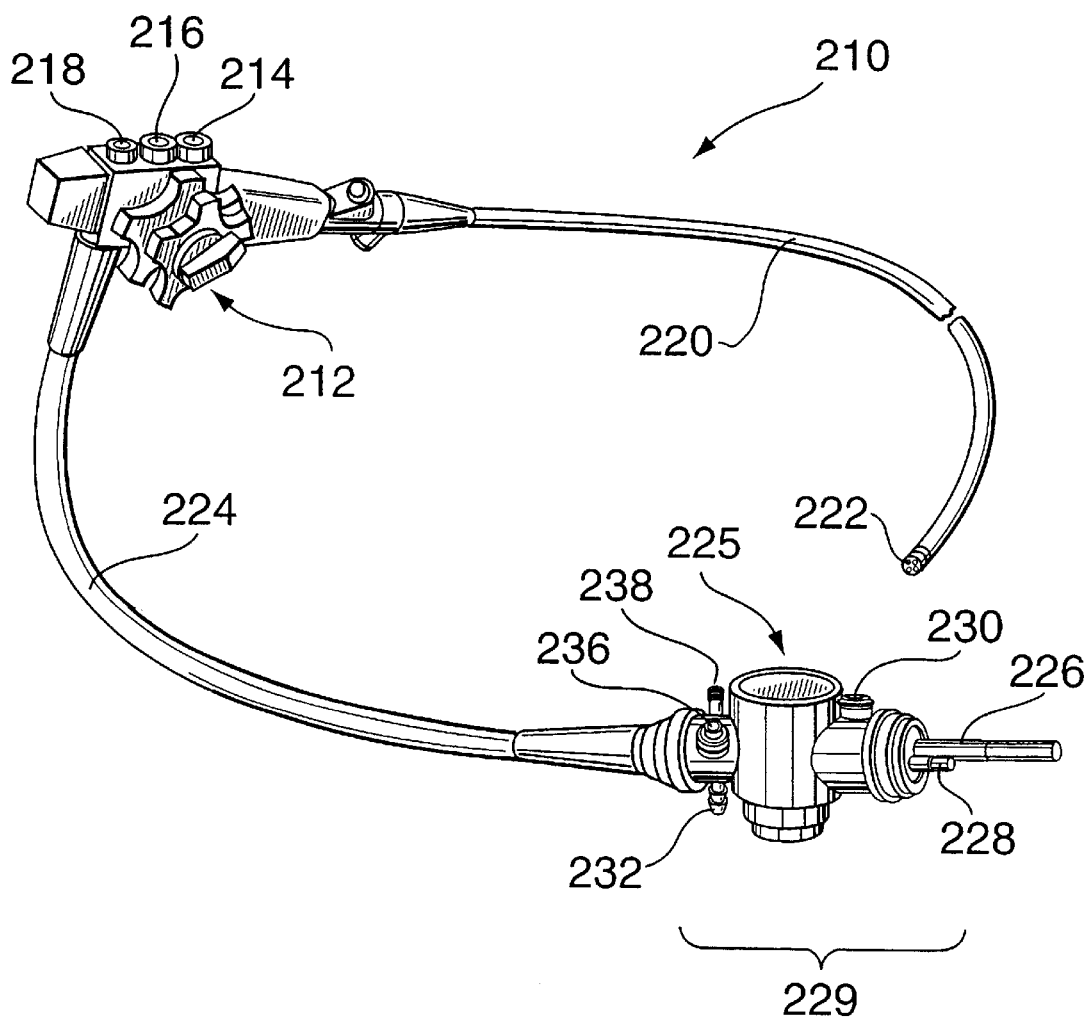
FIG. 1 shows an endoscope that is commonly known in the art.

Typically, in the preferred embodiment of the method according to the present invention a hollow endoscope is connected to a vessel, the endoscope-vessel combination placed in a sterilization chamber and sterilizing gas is exchanged between the chamber and the vessel through the endoscope. The exchange is effected by varying the pressure between the vessel and the sterilization chamber. Thus when the pressure in the sterilization chamber containing sterilizing gas is greater than the pressure in the vessel, the sterilizing gas is caused to pass through the internal passage of the endoscope into the vessel, thus permitting an effective sterilization of the internal passage of the endoscope. The terms gas or gaseous as used herein are to be construed broadly and include, for example, airborne droplets, airborne micro-particles and the like. The term air extends to any suitable gas or mixture thereof, for example nitrogen, carbon dioxide etc.

The method makes possible an effective sterilization of a hollow endoscope by selecting the volume of the vessel and the pressure difference between the sterilization chamber and the internal volume of the vessel, such that sterilizing gas passes through any internal passage in the endoscope. In a preferred embodiment, the pressure differential is between about half atmospheric pressure and a reduced pressure substantially less than atmospheric pressure. In this embodiment, the internal volume of the vessel should be the same as, or preferably larger than, the volume of the internal passage of the endoscope. The larger the difference in the volume between the vessel and the endoscope, the greater will be the volume of sterilizing gas passing through the internal passage when the pressure difference is effected. For example, in a further preferred embodiment, the sterilizing chamber is evacuated down to a pressure of 0.1 mbar and allowed to stabilize so that the pressure in the internal volume of the vessel will also be 0.1 mbar. The chamber is then filled with sterilizing gas and the pressure is allowed to rise to about half atmospheric pressure, thus creating a pressure difference between the internal volume of the vessel and the sterilizing chamber. In view of the pressure difference between the inside of the vessel and the chamber, a volume of sterilizing gas substantially equal to the internal volume of the vessel, will be drawn through the internal passage of the endoscope thus flushing the passage with the sterilizing gas.

However, the method may also be effected by using an overpressure of sterilizing gas. For example, if the pressure inside the sterilizing chamber is at atmospheric pressure, then the sterilizing gas may be introduced at such an overpressure that it flows through the internal passage of the endoscope into the vessel.

If the endoscope has more than one internal passage, then the internal volume of the vessel should be at least as great as, and preferably greater than, the combined volume of all the internal passages.

It is also possible for the vessel to be connected to more than one endoscope to form a multiple endoscope-vessel combination. In this case, the internal volume of the vessel should be equal to, or preferably greater than, the combined volume of all the internal passages of each endoscope.

The vessel is attached to the endoscope to form a sealed vessel-endoscope combination. Since the sterilization of the endoscope may be reduced or ineffective at the point of contact with the vessel, the vessel should be attached to the outside of the endoscope and preferably not too close to the end of the endoscope to ensure sterilization of the ends. Further, since endoscopes are usually designed with one end to enter the patient, the vessel is preferably attached to the end of the endoscope, which was not inserted into the patient.

Any suitable means of attachment may be used. Thus the vessel may have a neck which is clamped to the endoscope or the neck may be made of elastomeric material with an aperture slightly smaller than the outside diameter of the endoscope so the end of the endoscope can be pushed into the aperture which will naturally grip and seal with the endoscope. In one suitable embodiment, the vessel is cylindrical, of diameter several times larger than the diameter of the endoscope and having a closed end. The other end is formed into an inverted conical shape with the apex of the cone having the aperture and being within the cylindrical body of the vessel. Thus the end of the endoscope is guided towards the aperture by the inclined shape of the sides of the cone.

In a preferred sterilization procedure, the treatment is repeated. The first treatment is referred to as a first half-cycle and the second treatment as a second half-cycle or completion. That is, the first half-cycle may involve evacuation, then introducing sterilizing gas and allowing the pressure to rise to about half atmospheric pressure. Then the second half cycle would involve a repeat of those steps. That is the chamber and contents would again be evacuated, fresh sterilizing gas introduced and then allowing the pressure to rise to about half atmospheric pressure. Further such repetitions may be effected.

A function of the pressure differential between the internal volume of the vessel and the sterilization chamber is to ensure that sterilizing gas will flow into the internal passage of the endoscope. Any pressure differential may be used. However, for economy and convenience it is preferred to work between a higher pressure of about 500 to 525 mbar (about half atmospheric pressure) and a vacuum of from about 0.1 mbar to about 10 mbar, preferably 0.5 mbar to about 2 mbar. Thus it is preferred to operate at a pressure differential between the reduced pressure and the increased pressure of about half an atmosphere.

The vessel may be equipped with means to indicate the pressure within its internal volume or means to indicate the degree of sterilization. If such means includes visual indication, then a wall of the vessel, or a portion thereof, may be transparent, so that the means may be observed from outside the vessel. The means may also be connected to a remote monitoring device so that the pressure or sterilization could be monitored outside the sterilization chamber.

If ozone is used as the sterilizing gas, since ozone decomposes more rapidly at higher temperatures, it is preferred that the ozone would be at a temperature in the range of 20° C. to 35° C., more preferably 20° C. to 30° C. and particularly at around room temperature. To ensure effective sterilization, the ozone should also be adequately humidified.

The invention will be described with reference to an apparatus for generating ozone as the sterilizing gas. However, it should be understood that any sterilizing gas may be used.

Referring to FIG. 1, the prior art endoscope 210 illustrated has a control section 212 with the air/water valve 214 which, when its valve cover, not shown, is depressed, activates water feeding to a distal end 222 of an insertion tube 220. A suction valve 216, when its valve cover is depressed, activates suction from the distal end 222 of tube 220 and carbon dioxide, $CO_2$, gas valve 218, when depressed, connects lumens in the control section that insufflate noncombustible gas into the body cavity. The insertion tube 220 is inserted in the body cavity and the operator, using the control section 212, controls the flow of air, water, suction and gas to and from the body cavity. A universal cord 224 couples the control section 212 to a light guide connector section 225 that has a light guide 226 to be connected to a light source, an air pipe 228 and a water container connector 230 also has a suction connector 232 and other connectors 236 and 238 for such functions as a gas tube connector and a vent connector at the proximal end 229 of the endoscope 210. The endoscope 210 illustrated is of the flexible type however many different types of endoscope are available depending upon medical requirements, for example endoscopes with rigid endoscopic tubes. The present invention is not limited to any particular type of endoscope and the endoscope 210 may be regarded as a complex conduit(s).

Figure 2A:
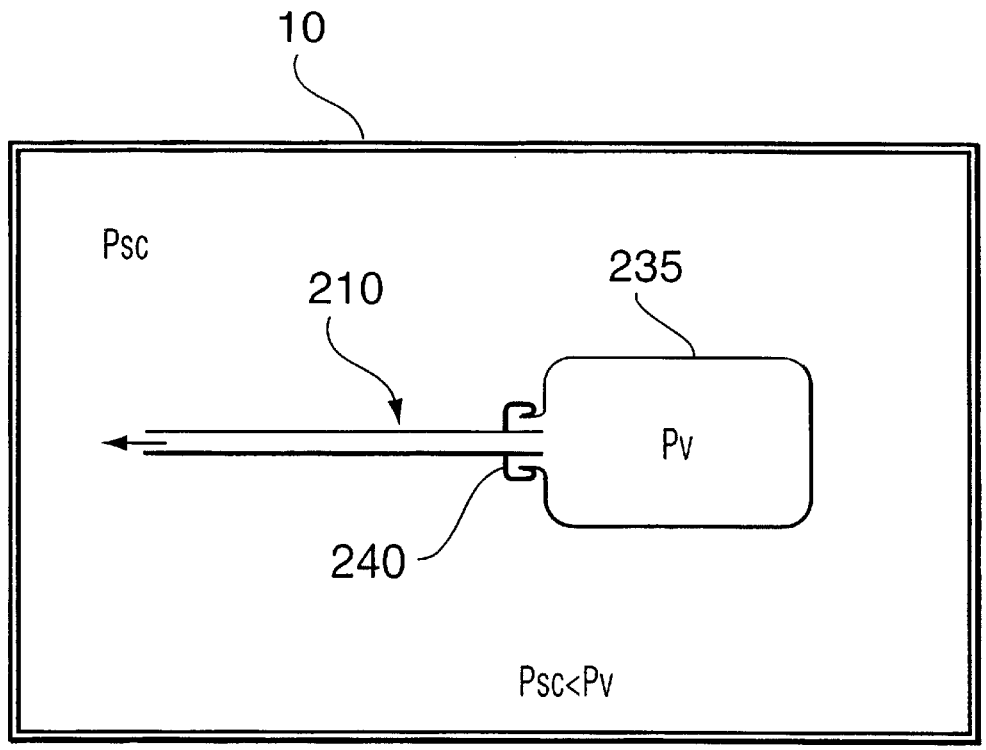
FIG. 2a shows a schematic cross-section through a preferred sterilization arrangement in accordance with the invention.

Referring to FIG. 2a, the endoscope sterilization method and arrangement according to one embodiment of the invention will be described in more detail. The hollow endoscope is sealed to an endoscope 210 as shown in a simplified fashion for ease of description, i.e., a conduit. The endoscope 210 is sealed in fluid communication with a vessel 235 forming an endoscope-vessel combination that is held within a sealed sterilisation chamber 10. Pressure within the sterilisation chamber and the vessel are indicated by Psc and Pv respectively. The vessel 235 has an opening that is provided with a seal allowing ready attachment and detachment of the endoscope. In operation, pressure within the sterilisation chamber is reduced, i.e., Psc<Pv. During the reduction in pressure, gas is drawn from the vessel 235 via the endoscope 210 conduit into the sterilising chamber 10 as indicated by an arrow until pressures within the sterilising chamber 10 and the vessel 235 are equilibrated, i.e., Psc=Pv.

Figure 2B:
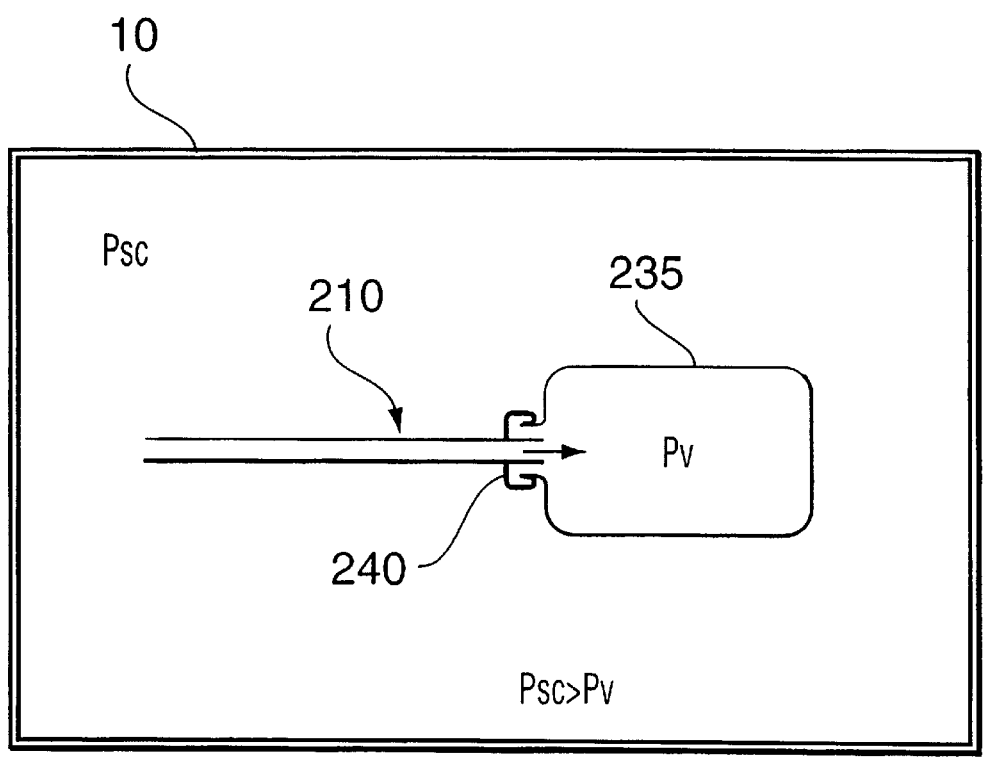
FIG. 2b shows a schematic cross-section through a preferred sterilization arrangement in accordance with the invention.

Referring to FIG. 2b, after the reduction in the pressure of the sterilising chamber 10 a gaseous sterilising mixture is provided, not shown, to the sterilisation chamber 10. The provision of the gaseous sterilising mixture to the sterilising chamber 10 results in an increase in the pressure within the sterilising chamber 10, Psc>Pv, and the gaseous sterilising mixture is drawn into the vessel 235 via the conduit(s) of the endoscope until pressures within the sterilising chamber 10 and the vessel 235 are equilibrated, i.e., Psc=Pv. Thus by effecting a pressure difference between the internal volume of the vessel and the sterilizing chamber, sterilizing gas is caused to flow through the internal passage of the endoscope 210. In this manner inner surfaces of the endoscope 210 have been subjected to sterilising conditions. Detailed above is a single sterilisation cycle and the number of cycles to which the endoscope 210 is subjected is varied according to requirements and parameters, namely type of sterilising gas, length of time of sterilising cycle, concentration of sterilising gas, type of endoscopic contamination present etc. As will be evident to one skilled in the art, it is possible to vary the order of pressure reduction or pressure increase within the chamber to achieve the same result. It is possible for the sterilising chamber to be charged at a positive pressure driving a sterilising gas from the sterilising chamber into the vessel 235 via the endoscope conduit(s). Nevertheless, a pressure reducing step is preferred over that of a step in which pressure within the sterilising chamber 10 is increased in excess of atmospheric pressure.

The sealing means 240 of the vessel 235 is not at the essence of the invention and many means of doing so will be evident to one skilled in the art. In one embodiment the vessel is equipped with an elastomeric septum, for example a Subraseal™, having a pre-bored hole of a smaller diameter than the distal end 222 of the endoscope 210 that covers the opening of the vessel 235. The distal end 222 of the endoscope 210 is inserted into the pre-bored hole such that the endoscope 210 is sealed in fluid communication with the vessel 235. Alternatively, the vessel is equipped with a screw top having a flexible gasket washer through which the distal end 222 of the insertion tube 220 is inserted and the screw top tightened such that the endoscope 210 is sealed in fluid communication with the vessel 235. The distal end 222 is one end of the endoscope and as one skilled in the art will recognize it is possible to seal either end of the conduit(s) in fluid communication with the vessel 235 for carrying out the method of the present invention.

Referring again to FIG. 1, sealing the distal end 222 in fluid communication with the vessel 235, to form an endoscope-vessel combination, provides an easier method of sterilising a plurality of conduits within the endoscope 210. This is because sterilising gas passes through the air pipe 228, the water container connector 230, the suction connector 232 and the other connectors 236 and 238 at the proximal end 229 of the endoscope 210. Nevertheless, it is within the scope of the present invention to attach a series of pipes to the air pipe 228, the water container connector 230, the suction connector 232 and the other connectors 236 and 238 respectively; the pipes being sealed in fluid connection with the vessel 235. Obviously, all supply and evacuation conduits leading to the unattached end 222 or preferably sealed in fluid connection with the vessel 235. It is also within the scope of the invention for different connectors at the proximal end to be sealed in fluid connection with more than one vessel 235.

The vessel 235 needs to be strong enough to withstand the pressures applied during the present method of endoscopic sterilisation and maintain the required volume to effect sterilization. The vessel 235 is made of any suitable material, for example a rigid material such as glass, or flexible or elastomeric materials such as PTFE™ (polytetrafluoroethylene) and polyethylene.

In a preferred embodiment the method of endoscope sterilisation described above is carried out in connection with a sterilising apparatus as described in the commonly assigned application Ser. No. 09/310,695 entitled "Method and Apparatus for Ozone Sterilization" and incorporated herein by reference. However, as one skilled in the art will appreciate, the method of endoscope sterilisation described above is applicable to many types of sterilisation chambers in which the pressure is variable. A suitable sterilisation chamber, is for example, a Sterrad™ unit made by Johnson & Johnson™. Other sterlization units are available from TS03™.

Figure 3:
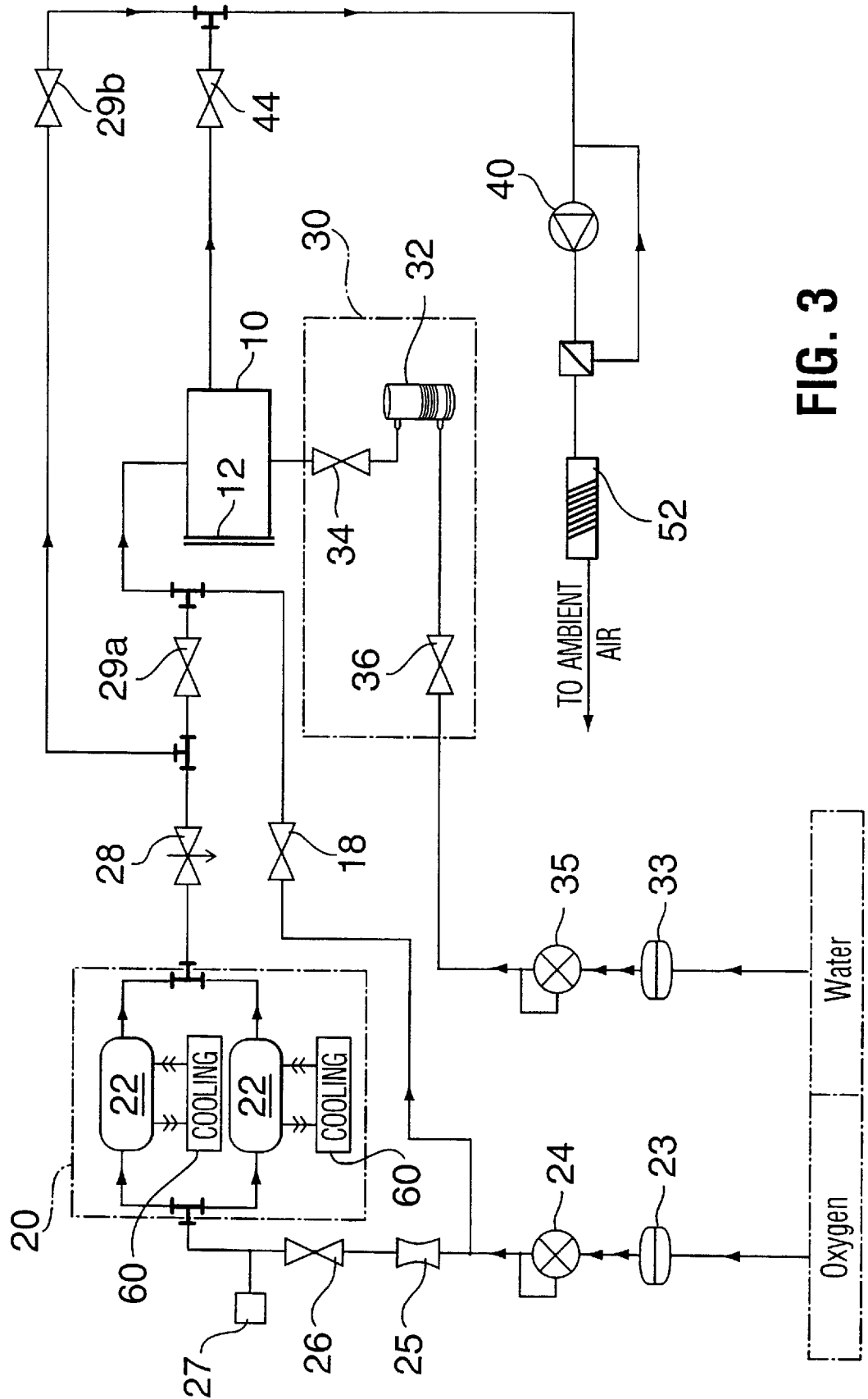
FIG. 3 shows a schematic illustration of a sterilization apparatus for use in a sterilization method in accordance with the invention.

An ozone sterilizer for use with the invention as illustrated schematically in FIG. 3 operates in a relatively simple manner. Medical quality oxygen is subjected in an ozone-generating unit 20 to an electrical field, which converts the oxygen into ozone. The ozone is then fed into a humidified sterilization chamber 10 where it sterilises medical devices. The ozone is subsequently reverted into oxygen using an ozone converting unit 52 containing an ozone converting catalyst. The only residues left at the end of the sterilization cycle are oxygen and clean water vapour.

Single cycle sterilization with ozone is more efficient, it provides for a shorter sterilization cycle than with EtO and requires few changes in user habits. Moreover, the ozone-based process in accordance with the invention is compatible for use with current packaging, such as sterile pouches and rigid containers.

An ozone sterilization method requires substantially no aeration or cooling down of sterilized instruments so that they can be used immediately following the sterilization cycle. This allows hospitals to reduce the cost of maintaining expensive medical device inventories. An ozone sterilization method offers several further advantages. It produces no toxic waste, does not require the handling of dangerous gas cylinders, and poses no threat to the environment or the user's health. Stainless-steel instruments and heat-sensitive instruments can be treated simultaneously, which for some users will obviate the need for two separate sterilizers.

A preferred sterilization apparatus suitable for use in accordance with the invention is illustrated schematically in FIG. 3. The apparatus includes a sterilization chamber 10 which can be sealed to contain a vacuum. This is achieved with an access door 12, which can be selectively opened for access into the chamber and which seals the chamber in the closed condition. The apparatus further includes an ozone generating unit 20 for supplying ozone-containing gas to the sterilization chamber, a humidifier arrangement 30 for supplying water vapour to the sterilization chamber, and a vacuum pump 40 (Trivac®, model D25BCS PFPE, manufacturer Leybold). The vacuum pump 40 is used for the application of a sufficient vacuum to the sterilization chamber 10 to increase the penetration of the sterilizing gas and to be able to generate water vapour at a temperature below the temperature inside the sterilization chamber. The vacuum pump 40 in the preferred embodiment is capable of producing a sufficient vacuum in the sterilization chamber to lower the boiling point of water in the chamber below the temperature in the chamber. In the preferred apparatus, the vacuum pump is capable of producing a vacuum of 0.1 mbar. Ozone produced in the ozone-generating unit 20 is destroyed by the ozone converting catalyst in ozone converting unit 52 to which ozone-containing gas is fed either after passage through the sterilization chamber 10 or directly from the ozone-generating unit 20 through valve 29b (optional). An example of an ozone converting catalyst is DEST 25, manufacturer TSO3. The ozone converting unit 52 is connected in series after the vacuum pump 40 to prevent ozone gas escaping to ambient. The ozone decomposing material in the preferred catalyst is carulite. For economic and practical reasons, it is preferred to use a catalyst for decomposition of the ozone in the sterilization gas exhausted from the sterilization chamber 10. The catalyst destroys ozone on contact and reverts it back into oxygen with a certain amount of heat being produced. Catalysts of this type and their manufacture are well known to a person skilled in the art of ozone generators and need not be described in detail herein. Furthermore, other means for destroying the ozone contained in the sterilization gas will be readily apparent to a person skilled in the art. For example, the gas can be heated for a preselected time to a temperature at which the ozone decomposition is accelerated, for example, to 300° C.

The humidifier arrangement 30 includes a humidifier chamber 32 (HUM 0.5, manufacturer TSO3) sealed to ambient and connected to the sterilization chamber 10 through a conduit and a vapour intake valve 34. The humidifier chamber 32 is equipped with a level control to ensure a sufficiently high water level, not shown. Water is directly supplied to the humidifier chamber 32 from a drinking or purified water supply connection. Water is supplied to the humidifier chamber 32 by way of a filter 33, a pressure regulator 35, and input valve 36. The water vapour produced in the humidifier chamber 32 enters the sterilization chamber 10 by way of a vapour intake valve 34.

The ozone-generating unit 20 includes a pair of ozone generators 22 (OZ, model 14a, manufacturer TSO3) of the corona discharge type, which are cooled to decrease the ozone decomposition rate, which is well known in the art. To achieve a good lethality rate in an ozone sterilization process, the amount of ozone supplied to the sterilization chamber should be sufficient to obtain a concentration of 48 to 96 milligram per liter preferably 60 to 72 milligram per liter. At these concentrations, the ozone generation is associated with a relatively high energy loss in the form of heat. Generally, about 95% of the supplied electrical energy is converted into heat and only 5% is used to produce ozone. Since heat accelerates the inverse transformation of ozone into oxygen, it must be removed as quickly as possible by cooling the ozone generators 22. The ozone generators in the above summarized apparatus are kept at the relatively low temperature of 3 to 6° C. by cooling system 60 which may be an indirect system with cooling water recirculation, or a direct cooling system with a refrigeration unit. The cooling system is preferably kept at the temperature of 3 to 6° C. In the preferred embodiment, the cooling system is kept at 4° C. so that the ozone-containing gas generated by unit 20 is at the ambient temperature around 20 to 35° C. Thus, the ozone-containing gas entering into the sterilization chamber for humidification and sterilization is kept at ambient temperatures of 20 to 35° C. This means that ozone decomposition is kept to a minimum and that the sterilization process is more efficient. This, provides a significant advantage over the apparatus of the prior art, since the temperature and pressure are maintained low throughout the sterilization cycle.

The ozone-generating unit is preferably supplied with medical quality oxygen. The apparatus can be connected to a wall oxygen outlet common in hospitals or to an oxygen cylinder or to any other source capable of supplying the required quality and flow. The supply of oxygen to the generators 22 takes place across a filter 23, a pressure regulator 24, a flow meter 25 and an oxygen shut off valve 26. The generators are protected against oxygen overpressure by a safety pressure switch 27. The ozone-oxygen mixture generated by the generators 22 is directed to the sterilization chamber 10 by a regulator valve 28 and a mixture supply solenoid valve 29a. The mixture can also be directly supplied to the ozone converting unit 52 by way of a bypass solenoid valve 29b (optional). In the preferred embodiment which includes a sterilization chamber of 125 liters volume, the pressure regulator 24 preferably controls the oxygen input at a flow rate of between about 1.5 and 2 liters per minute. However, it will be readily apparent to the skilled person that other flow rates may be used depending on the make and model of the ozone generators 22 and the size of the sterilization chamber.

Operation

Figure 4:
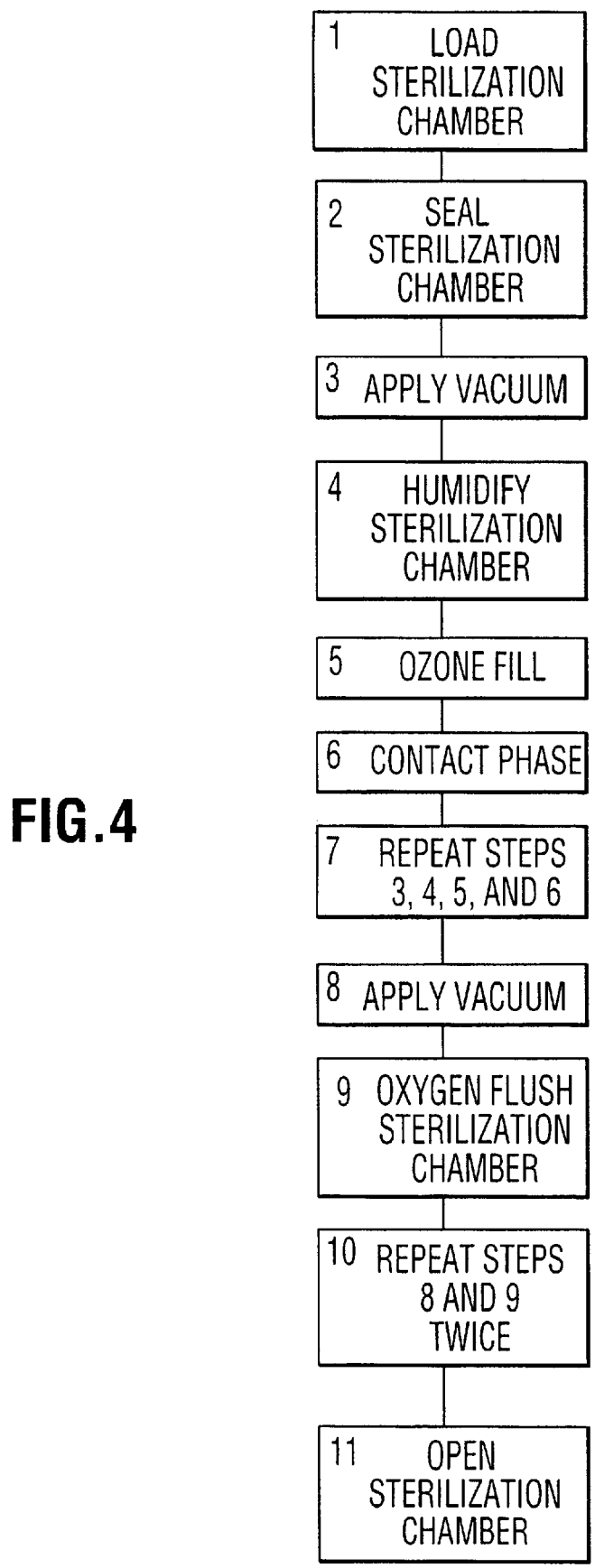
FIG. 4 is a flow diagram of a preferred sterilisation method in accordance with the invention.

The preferred sterilization method includes the following general steps as illustrated by the flow chart of FIG. 4. Step 1 is to load the sterilization chamber. Medical instruments including endoscopes to be sterilized are sealed in sterile packaging containers or pouches such as generally used in the hospital environment and then placed into the sterilization chamber. Steps 2 and 3 are sealing the sterilization chamber and applying a vacuum. The door of the sterilization chamber is closed and locked and the preconditioning phase is started by applying a vacuum to the sterilization chamber. In step 4 water vapour is admitted into the sterilization chamber to humidify the chamber contents. In steps 5 and 6 a mixture of ozone and oxygen is supplied to the chamber and the chamber maintained sealed for a preselected treatment period. In step 7 the vacuum application and ozone supply steps are preferably repeated at least once. To remove all remaining ozone in the sterilization chamber 10 when the sterilization cycle is completed, a ventilation phase begins with step 8 by applying a vacuum and flushing the chamber with oxygen in step 9. As shown in step 10, the vacuum and flushing steps 8 and 9 are repeated twice for a total of three oxygen flushes. The oxygen is allowed to fill the chamber 10 to atmospheric pressure each time. After the ventilation phase, the door is unlocked and the sterilized material can be taken out of the chamber.

Before the sterilization cycle begins, the humidifier chamber 32 is filled with water to an adequate level, which is sufficient to satisfy the requirements for the whole sterilization cycle. This is done by temporarily opening the water-input valve 36. Valve 36 remains closed for the whole remainder of the sterilization cycle. In the first phase of the sterilization cycle, oxygen intake valve 18, oxygen shut-off valve 26, mixture supply valve 29*a*, and mixture bypass valve 29*b* are closed and vapour intake valve 34, chamber drainage valve 44, and a bypass valve are opened. The sterilization chamber 10 is evacuated to a vacuum pressure of about 0.1 mbar. Water vapour inlet valve 34 closes when the absolute pressure in the sterilization chamber falls below 60 mbar. Once a pressure of about 1.0 mbar is achieved, the chamber drainage valve 44 closes and the vapour intake 34 opens to lower the pressure in the humidifier chamber 32 to the vacuum pressure in the sterilization chamber. That forces the water in the humidifier chamber to evaporate and to enter the sterilization chamber 10. Shortly before the end of the humidification period, usually about 2 to 6 minutes, the ozone generators are activated. The flow of the oxygen/ozone mixture exiting the ozone generator is controlled at all times by regulator valve 28 capable of resisting the vacuum and of adjusting the flow to between about 1.5 and 2 liters per minute. As an optional feature, the generators can be started at the same time as the humidification period begins. This is then achieved with shut-off valve 26 and mixture bypass valve 29*b*. Shut-off valve 26 opens to let oxygen enter the generators. The ozone-oxygen mixture produced by the generators is then guided directly into the ozone converting unit 50 through mixture bypass valve 29*b*. After a humidification period of approximately 30 minutes, the oxygen-ozone mixture is guided into the sterilization chamber by opening the mixture supply valve 29*a* and closing the mixture bypass valve 29*b*. The oxygen-ozone mixture enters the chamber 10 until an ozone concentration of 85 milligram per liter in the chamber is achieved. The time required for this step is dependent on the flow rate and concentration of the ozone gas in the mixture (preferably 10% to 12% by weight). At this point in time, the mixture supply valve 29*a* is closed to seal off the sterilization chamber and to maintain the humidified ozone/oxygen gas mixture in the chamber under vacuum.

Once the sterilization chamber is filled with the sterilization gas, mixture of oxygen and ozone gas, the generators 22 are stopped, the oxygen shut-off valve 26 is closed, and the ozone is maintained in contact with the articles to be sterilized for about 15 minutes, for a sterilization chamber of a volume of 125 liters (4 cubic feet). The length of this sterilization period varies with the volume of the sterilization chamber. At this stage, the sterilization chamber is still under the effect of a partial vacuum of about 500 to 525 mbar. In an optional second step, the pressure level is raised to about 900 mbar using oxygen as a filling gas. This pressure level is maintained for about 20 min. After the sterilization period, the vacuum is reapplied, preferably at a pressure of about 0.1 mbar again. Once the vacuum reaches 0.1 mbar, the humidification phase is recommenced, followed by the renewed injection of an oxygen/ozone sterilization gas mixture, followed by the sterilization period. The cycle of applying a vacuum of about 0.1 mbar, injecting sterilization gas, humidifying and sterilization period, can be repeated, and the number of repeat cycles, mini-cycles, selected to achieve complete sterilization of the instruments. The number of repeat cycles used in an experimental set-up of a method and apparatus of the type described above including a 125 liters (4 cubic foot) chamber was 2 repeat cycles. This set-up conformed to the Security Assurance Level standards of the FDA (SAL 10-6).

To remove all remaining ozone and humidity in the sterilization chamber 10 after complete sterilization a ventilation phase is engaged. The ventilation phase begins after the last sterilization period. The chamber drainage valve 44 opens and the vacuum is applied down to approximately 13 mbar. Vapour intake valve 34 closes when the pressure reaches 60 mbar to evacuate the remaining ozone in the humidifier. Once the vacuum pressure of 13 mbar is obtained, drainage valve 44 closes and the oxygen intake valve 18 opens, admitting oxygen into the sterilization chamber 10. Once atmospheric pressure is reached, the oxygen intake valve 18 is closed, the sterilization chamber drainage valve 44 opened, and vacuum reapplied until a pressure of 13 mbar is reached. The ventilation cycle is then repeated twice. Once the atmospheric pressure is reached after the last cycle, the door mechanism of the sterilization chamber is activated to permit access to the contents of the sterilization chamber. This ventilation phase has two functions. First, to remove all ozone residues in the sterilization chamber before opening the access door and, second, to dry the sterilized material by evaporation when the vacuum pressure is applied.

The ozone-containing gas evacuated from the sterilization chamber 10 is passed over the ozone decomposing catalyst of the ozone converting unit 52 prior to exhausting the gas to the atmosphere to ensure a complete decomposition of the ozone in the sterilization gas. The ozone converting unit 52 is used during only two portions of the sterilization cycle, the activation of the generators 22, with optional valves 26 and 29*b*, and the evacuation of the sterilization chamber 10. During the start up phase of the generators 22, the mixture bypass valve 29*b* is opened and the ozone is guided across the catalyst 52. Once the start-up phase of the generators 22 is complete, the bypass valve 29*b* closes. During evacuation of the sterilization chamber 10, the sterilization chamber drainage valve 44 is opened and the ozone containing sterilization waste gas guided to the catalyst 52. Once the evacuation of the sterilization chamber 10 is completed, the drainage valve 44 is closed. The circulation of ozone is ensured by the vacuum pump 40, which operates during the whole sterilization cycle including all repeat cycles.

Oxygen/ozone-containing sterilization gas is injected into the humidified sterilization chamber at ambient temperature. The ozone-containing gas is not heated. For optimum operation of a sterilizer having a 125 liter chamber, a system is preferably used which is capable of generating an ozone flow of between about 1.5 and 2 liters per minute containing about 85 mg/l of ozone to obtain at least at total of 9000 mg of ozone for each of the fillings of the sterilization chamber.

In another preferred process, humidification of the sterilization chamber is carried out by a pair of atomizers. The water is supplied to each of the atomizers from a water tank hooked up to the drinking water supply or a purified water supply. Ozone is supplied to the atomizers from an ozone accumulation tank. The atomizers are made of ozone oxidation resistant material, and are installed directly in the sterilization chamber. When the vacuum level is reached in the sterilization chamber, the atomizers release water and ozone. The ozone is moistened inside the atomizer. The ozone/atomized water mixture penetrates the sterilization chamber. Injecting the water into the sterilization chamber under vacuum has the immediate effect of evaporating the water. The sterilization chamber operating temperature is 20 to 35° C., a temperature at which water evaporates at pressures of 23.3 to 56.3 mbar. Thus, the water becomes vapour due to the vacuum created by the vacuum pump. The resulting ozone/water vapour mixture penetrates the material to be sterilized.

Changes and modifications in the specifically described embodiments can be carried out without departing from the scope of the invention which is intended to be limited only by the scope of the appended claims.

What is claimed is:

1. A method for sterilizing within a sterilization chamber a hollow endoscope having a proximal end, a distal end and an internal passage there between, the method comprising the steps of:
   (i) sealing one end of said proximal and distal ends of the endoscope to a sealed vessel for fluid communication between the passage and the vessel to form an endoscope-vessel combination;
   (ii) disposing the endoscope-vessel combination within the sterilization chamber such that the other end of said proximal and distal ends is in fluid communication with the sterilization chamber;
   (iii) supplying a sterilization gas to the sterilization chamber;
   (iv) effecting a pressure difference between the internal volume of the vessel and the sterilizing chamber, such that the pressure in the internal volume of the vessel is below the pressure in the sterilization chamber whereby the vessel, upon exposure to the pressure difference, maintains an internal volume for causing sterilizing gas supplied to the sterilizing chamber to flow through the internal passage of the endoscope into the vessel.

2. A method for sterilizing an endoscope according claim 1, wherein the endoscope is sealed to the vessel at said distal end.

3. A method for sterilizing an endoscope according to claim 1, wherein the pressure difference is effected by reducing the pressure in the sterilization chamber so that the internal volume of the vessel is at a reduced pressure followed by introducing sterilizing gas at an increased pressure into the sterilizing chamber.

4. A method for sterilizing an endoscope according to claim 1, wherein the step (iv) is repeated at least once.

5. A method according to claim 1 wherein the vessel includes means to monitor the pressure of the internal volume of the vessel.

6. A method according to claim 5 wherein the vessel has a transparent portion in a wall thereof to observe the monitoring means.

7. A method according to claim 3 wherein said increased pressure is about atmospheric pressure.

8. A method according to claim 3 wherein the difference between said reduced pressure and said increased pressure is about 1 atmosphere.

9. A method according to claim 1 wherein the sterilizing gas is humidified ozone.

10. A method according to claim 3 wherein the sterilizing gas is humidified ozone.

11. A method according to claim 3 wherein said reduced pressure is from about 0.1 mbar to about 10 mbar.

12. A method according to claim 3 wherein said reduced pressure is from about 0.5 mbar to about 2 mbar.

13. A method according to claim 10 wherein the ozone has a humidity of from 95 to 100%.

14. A method according to claim 1 wherein the end of the endoscope which is sealed in fluid communication with said vessel, protrudes into said vessel.

15. A method for sterilizing within a sterilization chamber a hollow endoscope having a distal end, a proximal end and an internal passage there between which has an internal volume, the method comprising the steps of:
   (i) providing a sterilization chamber;
   (ii) sealing one end of said proximal and distal ends of the endoscope in fluid communication with a substantially closed vessel to form an endoscope-vessel combination, said vessel having an internal volume larger than the internal volume of the endoscope;
   (iii) placing the endoscope-vessel combination into the sterilization chamber such that the other end of said proximal and distal ends is in fluid communication with the sterilization chamber;
   (iv) sealing the sterilization chamber;
   (v) applying a vacuum of a preselected vacuum pressure to the sterilization chamber;
   (vi) supplying an amount of water vapour to the sterilization chamber for humidifying the sterilization chamber;
   (vii) supplying ozone to the sterilization chamber at a higher pressure than said pre-selected vacuum pressure to obtain a pressure difference between the pressure of the internal volume of the vessel and the pressure of the sterilization chamber, said ozone being sufficient to sterilize the endoscope and the internal passage of the endoscope; and
   (viii) maintaining the endoscope, the internal volume of the endoscope and the internal volume of the vessel in contact with the ozone for a preselected treatment period to sterilize the endoscope whereby the vessel, upon exposure to the pressure difference, maintains an internal volume for causing the ozone supplied to the sterilization chamber to flow through the internal passage of the endoscope into the vessel.

16. A method according to claim 15 wherein the difference between said preselected vacuum pressure and said higher pressure is about half an atmosphere.

* * * * *